US012767685B2

(12) United States Patent
Okarvi et al.

(10) Patent No.: US 12,767,685 B2
(45) Date of Patent: Oct. 20, 2026

(54) METHOD OF PREPARING ESTRADIOL DERIVATIVES BY SOLID-PHASE SYNTHESIS

(71) Applicant: KING FAISAL SPECIALIST HOSPITAL & RESEARCH CENTRE, Riyadh (SA)

(72) Inventors: Subhani M. Okarvi, Riyadh (SA); Ibrahim Al-Jammaz, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 562 days.

(21) Appl. No.: 18/378,303

(22) Filed: Oct. 10, 2023

(65) Prior Publication Data

US 2024/0116978 A1 Apr. 11, 2024

(30) Foreign Application Priority Data

Oct. 10, 2022 (EP) ..................................... 22200607

(51) Int. Cl.
*C07J 1/00* (2006.01)
*A61K 51/04* (2006.01)
*C07B 59/00* (2006.01)

(52) U.S. Cl.
CPC ......... *C07J 1/0022* (2013.01); *A61K 51/0482* (2013.01); *A61K 51/0493* (2013.01); *C07B 59/007* (2013.01); *C07J 1/0011* (2013.01); *A61K 2121/00* (2013.01); *A61K 2123/00* (2013.01); *C07B 2200/05* (2013.01)

(58) Field of Classification Search
CPC ... C07J 1/0022; C07J 1/0011; A61K 51/0482; A61K 51/0493; A61K 2121/00; C07B 59/007
See application file for complete search history.

(56) References Cited

U.S. PATENT DOCUMENTS 10,695,450 B2 * 6/2020 Viot ........................ C07B 63/00

FOREIGN PATENT DOCUMENTS

| | | | |
|---|---|---|---|
| CN | 109942662 | A | 6/2019 |
| WO | 2006/107794 | A2 | 10/2006 |
| WO | 2006/107794 | A3 | 10/2006 |

OTHER PUBLICATIONS

Banerjee, Sharmila et al. "An estradiol-conjugate for radiolabelling with 177Lu: an attempt to prepare a radiotherapeutic agent." Bioorganic & Medicinal Chemistry, 13(13):4315-4322, (Year: 2005).
Bolt, H. M., "Metabolism of Estrogens-Natural and Synthetic." Pharmac. Ther. vol. 4:155-181, (Year: 1979).
Mankoff, David A. et al. "Tumor Receptor Imaging." The Journal of Nuclear Medicine 49(6):149S-163S, Jun. 2008.
Yang, Xin-Bin et al. "Synthesis, DNA binding and cleavage activities of the copper (II) complexes of estrogen-macrocyclic polyamine conjugates." Bioorganic & Medicinal Chemistry 16(7): 3871-3877, (Year: 2008).

* cited by examiner

*Primary Examiner* — Sikarl A Witherspoon
(74) *Attorney, Agent, or Firm* — SALIWANCHIK, LLOYD & EISENSCHENK

(57) ABSTRACT

The present invention relates to a method of preparing estradiol derivatives and/or estrone derivatives, which are suitable for radiolabeling. The present invention further relates to the estradiol derivatives and/or estrone derivatives, preferably obtained by the method of the present invention, as well as to the use of the estradiol derivatives and/or estrone derivatives for radiolabeling with diagnostic and/or therapeutic radionuclides. The present invention further relates to a method of imaging and/or diagnosis of breast cancer as well as to a method of treatment of breast cancer.

28 Claims, 9 Drawing Sheets

5

6

1,4,7,10-Tetraazacyclododecane-
1,4,7-triacetic acid
Estradiol lysine 1,4,7-Triazacyclononane-
1,4,7-triacetic acid 7
Aminooxyacetic acid

METHOD OF PREPARING ESTRADIOL DERIVATIVES BY SOLID-PHASE SYNTHESIS

CROSS-REFERENCE TO A RELATED APPLICATION

This application claims priority to European Patent Application No. 22200607.4, filed Oct. 10, 2022.

FIELD OF THE INVENTION

The present invention relates to a method of preparing estradiol derivatives and/or estrone derivatives, which are suitable for radiolabeling. The present invention further relates to the estradiol derivatives and/or estrone derivatives, preferably obtained by the method of the present invention, as well as to the use of the estradiol derivatives and/or estrone derivatives for radiolabeling with diagnostic and/or therapeutic radionuclides. The present invention further relates to a method of imaging and/or diagnosis of breast cancer as well as to a method of treatment of breast cancer.

BACKGROUND OF THE INVENTION

The development of new radiopharmaceuticals for clinical application in personalized nuclear medicine with PET (positron-emission tomography) and SPECT (single-photon emission tomography) has experienced great progress over the last decade, which is reflected in the large and still growing number of potent radiopharmaceuticals used for diagnostic imaging and therapy of different diseases. A tendency that can be seen toward PET radiotracers development is the use of radiolabeled targeting vectors that accumulate with high efficiency and specificity at the target receptor site (i.e., tumors), allowing a highly sensitive and precise target visualization (tumor detection). Many of these vectors are small bioactive molecules generally having fast pharmacokinetics matching well with the radionuclides of appropriate half-lives to fully exploit the potential of these targeting vectors for diagnostic imaging and targeted radionuclide therapy (Lau et al., 2020; Fani et al., 2012).

Estrogen-receptor (ER) status is important in breast cancer for risk assessment and predicting response to therapy. Both the US National Comprehensive Cancer Network (NCCN) and the American Society of Clinical Oncology (ASCO) recommend ER testing of lesions in any primary or newly metastatic breast cancer. Approximately 75% of all breast cancers in women, and 99% in men, are ER-positive, thus the measurement of the estrogen-receptor content of human breast tumors has proved useful in selecting the most suitable form of treatment for metastatic disease (Gradishar et al., 2020; Allison et al., 2020; Blamey et al., 2010; Cardoso et al., 2018). In general, tumors devoid of estrogen-receptor are not responsive to hormonal therapy, whereas those that contain receptors have a greater response rate than unselected cases (Thompson et al., 1979; Allegra 1979). It has been shown that estrogen promotes cell proliferation and inhibits apoptosis through a complex signaling cascade resulting in transcriptional changes that may include the modulation of tumor suppressor function. Since the estrogen-receptor is a protein that binds estrogens with high affinity, it also provides a potential mechanism for the selective accumulation of estrogens within receptor-positive tumors (Thompson et al., 1979; Allegra 1979; Kiesewetter et al., 1984).

Nonetheless, it is a known fact that if cancer can be diagnosed at an early stage and characterized for ER status and metastatic state, then patients can show improved outcomes with appropriate treatment (Nayak et al., 2008; Bafaloukos et al., 2005; Veronesi et al., 2005). As a result, in the past two decades, greater emphasis has been placed on the development of nuclear imaging approaches for breast and other cancers that are based on either SPECT or PET (Katzenellenbogen et al., 1997; Katzenellenbogen et al., 2020). Whole-body imaging is possible with PET and SPECT and therefore offers a precise noninvasive approach for assessing regional and disseminated cancers. Thus, in principle, a radiolabeled estrogen derivative with suitable biochemical, binding, and pharmacokinetic properties could act as an imaging or therapeutic agent for such receptor-positive tumors (Nayak et al., 2008).

In the last two decades, several $^{99m}$Tc-labeled estradiol-based compounds were prepared and evaluated due to the widespread availability of $^{99m}$Tc (technetium-99m) generators, low comparative cost, and a half-life of 6 hours. The first $^{99m}$Tc-labeled estradiol was developed as early as 1991 by introducing the $N_2S_2$ (diamine-dithiol) donor atom set to coordinate the technetium through the Tc(V)monooxo core (DiZio et al., 1991). Furthermore, the development of analogous 186/188Re compounds for therapy is an additional advantage. Consequently, many groups have pursued the objective of developing a $^{99m}$Tc-labeled estradiol derivative. A major limitation of such an approach was the inability to yield high specific activity tracers and other labeling approaches using different Tc cores were applied by different groups (Katzenellenbogen et al., 2020; DiZio et al., 1991; Ramesh et al., 2006; Xia et al., 2016; Tejeria et al., 2017). Subsequent efforts have been directed towards developing other methods for radiolabeling estrogen imaging agents with the widely available radionuclide $^{99m}$Tc for SPECT, through both pendant- and integrated-chelate approaches (Kiesewetter et al., 1984, Katzenellenbogen et al., 2020; DiZio et al., 1991; Ramesh et al., 2006; Xia et al., 2016; Tejeria et al., 2017. Additionally, both steroidal and non-steroidal estrogen derivatives were prepared and radiolabeled with $^{99m}$Tc (SPECT) and $^{94m}$Tc (PET) for ER imaging. However, the agents described to date have demonstrated suboptimal target tissue selectivity in vivo, possibly as a result of the high lipophilicity or rapid metabolism of these agents. Furthermore, the complex chemistry involved in the radiosynthesis of these compounds to obtain high yields and purities has further limited their development for clinical use (Katzenellenbogen et al., 2020; DiZio et al., 1991; Ramesh et al., 2006; Xia et al., 2016; Tejeria et al., 2017).

In the past few years, attention has been directed towards the development of PET-based estradiol derivatives because PET radiopharmaceuticals offer increased accuracy, better sensitivity, and inherently better image resolution over SPECT radiopharmaceuticals (Katzenellenbogen et al., 2020; Shi et al., 2014; Brookes 2021). Several $^{18}$F-labeled estrogen derivatives were tested in animals and shown to demonstrate ER selectivity (Katzenellenbogen et al., 2020). The most successful $^{18}$F-labeled estrogen derivative, $^{18}$F-fluoroestradiol ([$^{18}$F]-FES), a steroid-based PET tracer, has been evaluated clinically, with promising results for the imaging of estrogen-binding tumors and for predicting the responsiveness of breast tumors to antiestrogen drugs such as tamoxifen (Katzenellenbogen et al., 2020]. The role of estrogen in endometrial carcinogenesis has been well documented, and successful applications of $^{18}$F-FES have been reported for endometrial and other gynecologic cancers. In addition, many studies have suggested that [$^{18}$F]FES can be used as a valuable PET tracer to determine the tissue levels of ER in patients with breast cancer and may emerge as a valuable tool to predict which patients with primary, recurrent, or metastatic breast or metastatic breast cancer will respond to hormone therapy (Brookes 2021; CERIANNA™—Reference ID: 4610145-Accessdata.fda.gov).

As mentioned before, [$^{18}$F]-FES (FIG. 1) is known as a clinically important tracer in nuclear medicine as an estrogen receptor ligand for investigating primary and metastatic breast cancers. Recently US FDA has approved [$^{18}$F]-FES (Cerianna) as a radioactive diagnostic agent indicated for PET imaging for the detection of ER-positive lesions as an adjunct to biopsy in patients with recurrent or metastatic breast cancer (Brookes 2021; CERIANNA™—Reference ID: 4610145 Accessdata.fda.gov).

There is a need in the art for improved means and methods for synthesizing estradiol derivatives, in particular conjugated estradiol derivatives which allow labeling.

SUMMARY OF THE INVENTION

According to the present invention this object is solved by a method of preparing an estradiol derivative and/or an estrone derivative for radiolabeling, comprising the steps of (1) preparing an acetic acid-estradiol precursor;

(2) coupling the acetic acid-estradiol precursor obtained in step (1) to a solid phase synthesis resin, wherein said resin is suitable for Fmoc (9-fluorenylmethyl-oxycarbonyl)-solid phase synthesis and carries Fmoc-lysine with a protecting group at the lysine side chain;

(3) removing the protecting group at the lysine side chain;

(4) coupling a bifunctional group for radiolabeling to the lysine side chain; and (5) removal of the estradiol derivative and/or the estrone derivative from the resin.

According to the present invention this object is solved by an estradiol derivative selected from DOTA-estradiol, NOTA-estradiol and AoA-estradiol.

According to the present invention this object is solved by an estrone derivative selected from DOTA-estrone, NOTA-estrone and AoA-estrone.

According to the present invention this object is solved by using the estradiol derivative of the present invention for radiolabeling with one or more diagnostic and/or therapeutic radionuclides.

According to the present invention this object is solved by using the estrone derivative of the present invention for radiolabeling with one or more diagnostic and/or therapeutic radionuclides.

According to the present invention this object is solved by a method of imaging and/or diagnosis of breast cancer, comprising the step of:

administering a diagnostic amount of an estradiol derivative of the present invention or diagnostic amount of an estrone derivative of the present invention to a subject.

According to the present invention this object is solved by a method of treatment of breast cancer, comprising the step of:

administering a therapeutic amount of an estradiol derivative of the present invention or a therapeutic amount of an estrone derivative of the present invention to a subject in need thereof.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "18 to 30" should be interpreted to include not only the explicitly recited values of 18 to 30, but also include individual values and sub-ranges within the indicated range. Thus, included in this numerical range are individual values such as 18, 19, 20, 21 . . . 29, 30 and sub-ranges such as from 20 to 28, 20 to 25, 21 to 24, 7 to 9 etc. This same principle applies to ranges reciting only one numerical value, such as below 25". Furthermore, such an interpretation should apply regardless of the breadth of the range or the characteristics being described.

Preparation Method for Estradiol and/or Estrone Derivatives

As outlined above, the present invention provides a method of preparing estradiol derivatives. As outlined above, the present invention provides a method of preparing estrone derivatives.

Said estradiol derivatives are suitable for radiolabeling. Said estrone derivatives are suitable for radiolabeling.

Said method comprises the steps of (1) preparing an acetic acid-estradiol precursor;

(2) coupling the acetic acid-estradiol precursor obtained in step (1) to a solid phase synthesis resin, wherein said resin is suitable for Fmoc (9-fluorenylmethyl-oxycarbonyl)-solid phase synthesis and carries Fmoc-lysine with a protecting group at the lysine side chain;

(3) removing the protecting group at the lysine side chain;

(4) coupling a bifunctional group for radiolabeling to the lysine side chain; and (5) removal of the estradiol derivative and/or the estrone derivative from the resin.

Step (1)

In step (1), an acetic acid-estradiol precursor is prepared.

In one embodiment, step (1) comprises reacting estrone and tert-butyl bromoacetate.

Estrone and tert-butyl bromoacetate are preferably reacted in the presence of potassium carbonate ($K_2CO_3$) and potassium iodide (KI).

Preferably, at the end of step (1) the tert-butyl protecting group is removed from the acetic acid-estradiol precursor.

Step (2)

In step (2), the acetic acid-estradiol precursor obtained in step (1) is coupled to a solid phase synthesis resin, which is suitable for Fmoc (9-fluorenylmethyl-oxycarbonyl)-solid phase synthesis.

A preferred solid phase synthesis resin is Wang resin.

Said resin, preferably Wang resin, is suitable for Fmoc (9-fluorenylmethyl-oxycarbonyl)-solid phase synthesis and carries Fmoc-lysine with a protecting group at the lysine side chain;

The protecting group at the Lys side chain resin is preferably ivDde (4,4-dimethyl-2,6-dioxocyclohex-1-ylidene)-3-methylbutyl-).

The resin used in step (2) is preferably Fmoc-Lys(ivDde)-Wang resin.

In a preferred embodiment, before the coupling of step (2), the acetic acid-estradiol precursor is preactivated at its α-carboxylic function by using an activating reagent.

The activating reagent is preferably HBTU (O-benzotriazol-1-yl)-1,1,3,3-tetramethyluronium hexafluorophosphate) which is used in the presence of a base, preferably DIEA (diisopropylethylamine).

The coupling to the resin comprises the removal of the Fmoc-protecting group such that the activated acetic acid-estradiol precursor can react with the resin-bound N-terminal amino group of lysine.

Completion of the coupling can be confirmed, such as via Kaiser ninhydrin test, as known to the skilled artisan.

Step (3)

In step (3), the protecting group at the lysine side chain is removed.

In the embodiment, where the protecting group at the lysine side chain is ivDde, ivDde is removed via treatment with hydrazine monohydrate.

Step (4)

In step (4), a bifunctional group for radiolabeling is coupled to the lysine side chain.

The bifunctional group for radiolabeling is preferably selected from

- DOTA (1,4,7,10-tetraazacyclododecane-1,4,7,10-tetraacetic acid),
- NOTA (1,4,7-triazacyclononane-1,4,7-triacetic acid) and
- AoA (aminooxy acetic acid).

Preferably, in step (4) for coupling the bifunctional group for radiolabeling to the Lys side chain DOTA-tris-(t-Bu ester), NOTA-bis-(t-Bu ester) or Boc-AoA is used, wherein said DOTA-tris-(1-Bu ester), NOTA-bis-(t-Bu ester) or Boc-AoA is preferably preactivated, preferably with HBTU and DIEA.

Completion of the coupling can be confirmed, such as via Kaiser ninhydrin test, as known to the skilled artisan.

Step (5)

In step (5), the estradiol derivative or the estrone derivative is removed or cleaved from the resin and the estradiol derivative or the estrone derivative is obtained.

Preferably, said cleavage is carried with a cleavage cocktail, wherein such cleavage cocktails are known to the skilled artisan.

A preferred example is a cleavage cocktail comprising trifluoroacetic acid (TFA), such as TFA/triisopropylsilane/water (e.g. 95%: 2.5%: 2.5%, v/v).

Preferably at least one of steps (1) to (5) is carried out at a temperature in the range from about 18 to about 30° C., more preferably from about 20 to about 25° C., even more preferably at ambient temperature, such as at about 23° C.

In one embodiment, all steps are carried out at a temperature in the range from about 18 to about 30° C., more preferably from about 20 to about 25° C., even more preferably at ambient temperature, such as at about 23° C.

In a preferred embodiment, the method of the present invention further comprises the step of (6) radiolabeling the estradiol derivative obtained in step (5) with a diagnostic and/or therapeutic radionuclide and/or diagnostic radiotracer(s);

or (6) radiolabeling the estrone derivative obtained in step (5) with a diagnostic and/or therapeutic radionuclide and/or diagnostic radiotracer(s).

Examples for diagnostic and/or therapeutic radionuclides are $^{68}$Ga, $^{177}$Lu, $^{64}$Cu, $^{89}$Zr, $^{18}$F.

Radiolabeling with $^{18}$F can also be with $^{18}$F-FBA (fluorobenzaldehyde).

Radiolabeling with a diagnostic radiotracer can also be with a radiotracer comprising $^{18}$F, such as with $^{18}$FDG (fluorodeoxyglucose).

Preferably, DOTA and NOTA-conjugated estradiol derivatives are radiolabeled with one or more diagnostic and/or therapeutic radionuclides, such as $^{68}$Ga, $^{177}$Lu, $^{64}$Cu, $^{89}$Zr.

Preferably, AoA-estradiol is radiolabeled with $^{18}$F or $^{18}$FDG (fluorodeoxyglucose). AoA-estradiol is preferably radiolabeled via oxime functionality.

Preferably, DOTA and NOTA-conjugated estrone derivatives are radiolabeled with one or more diagnostic and/or therapeutic radionuclides, such as $^{68}$Ga, $^{177}$Lu, $^{64}$Cu, $^{89}$Zr.

Preferably, AoA-estrone is radiolabeled with $^{18}$F or $^{18}$FDG (fluorodeoxyglucose). AoA-estrone is preferably radiolabeled via oxime functionality.

Estradiol Derivatives, Estrone Derivatives and their Uses

As outlined above, the present invention provides an estradiol derivative selected from

- DOTA-estradiol,
- NOTA-estradiol and
- AoA-estradiol,

In a preferred embodiment, the estradiol derivative is selected from

- DOTA-estradiol-lysine
- NOTA-estradiol-lysine
- and
- AoA-estradiol-lysine.

DOTA-estradiol-lysine: 2,2',2"-(10-(2-((5-(((1S,3aS,3bR,9bS,11 aS)-11a-Methyl-2,3,3a,3b,4,5,9b,10,11,11a-decahydro-1H-cyclopenta[a]phenanthrene-1-ol-7-oxy)-Acetamido)(5-carboxyl)pentanyl)amino)-2-oxoethyl)-1,4,7,10-tetraazacyclododecane-1,4,7-triyl)triacetic acid.

NOTA-estradiol-lysine: 2,2'-(7-(2-((5-(((1S,3aS,3bR,9bS,11 aS)-11a-Methyl-2,3,3a,3b,4,5,9b,10,11,11a-decahydro-1H-cyclopenta[a]phenanthrene-1-ol-7-oxy)-Acetamido)(5-carboxyl)pentanyl)amino)-2-oxoethyl)-1,4,7-triazacyclononane-1,4-diyl)diacetic acid.

AoA-estradiol-lysine: 2-(((1S,3aS,3bR,9bS,11aS)-11a-Methyl-2,3,3a,3b,4,5,9b,10,11,11a-decahydro-1H-cyclopenta[a]phenanthrene-1-ol-7-oxy)-Acetamido)-6-(aminooxyacetamido)-hexanoic acid.

As outlined above, the present invention provides an estrone derivative selected from

- DOTA-estrone,
- NOTA-estrone and
- AoA-estrone,

In a preferred embodiment, the estradiol derivative is selected from

- DOTA-estrone-lysine
- NOTA-estrone-lysine
- and
- AoA-estrone-lysine.

In a preferred embodiment, the estradiol derivative of the present invention further comprises one or more diagnostic and/or therapeutic radionuclide and/or a diagnostic radiotracer.

In a preferred embodiment, the estrone derivative of the present invention further comprises one or more diagnostic and/or therapeutic radionuclide and/or a diagnostic radiotracer.

As discussed above, examples for diagnostic and/or therapeutic radionuclides are $^{68}$Ga, $^{177}$Lu, $^{64}$Cu, $^{89}$Zr and $^{18}$F.

An estradiol derivative radiolabeled with $^{18}$F can also be an estradiol derivative radiolabeled with $^{18}$F-FBA (fluorobenzaldehyde).

An estrone derivative radiolabeled with $^{18}$F can also be an estradiol derivative radiolabeled with $^{18}$F-FBA (fluorobenzaldehyde).

As discussed above, an example for a diagnostic radiotracer is $^{18}$FDG (fluorodeoxyglucose).

Preferably, DOTA and NOTA-conjugated estradiol derivatives are radiolabeled with one or more diagnostic and/or therapeutic radionuclides, such as $^{68}$Ga, $^{177}$Lu, $^{64}$Cu and $^{89}$Zr.

Preferably, AoA-estradiol is radiolabeled with $^{18}$F or $^{18}$FDG (fluorodeoxyglucose).

Preferably, DOTA and NOTA-conjugated estrone derivatives are radiolabeled with one or more diagnostic and/or therapeutic radionuclides, such as $^{68}$Ga, $^{177}$Lu, $^{64}$Cu and $^{89}$Zr.

Preferably, AoA-estrone is radiolabeled with $^{18}$F or $^{18}$FDG (fluorodeoxyglucose).

In a preferred embodiment, the estradiol derivative of the present invention is obtained by a method of the present invention.

In a preferred embodiment, the estrone derivative of the present invention is obtained by a method of the present invention.

The present invention further provides the use of an estradiol derivative of the present invention or of an estradiol derivative obtained by a method of the present invention for radiolabeling with one or more diagnostic and/or therapeutic radionuclide and/or with a diagnostic radiotracer.

The present invention further provides the use of an estrone derivative of the present invention or of an estrone derivative obtained by a method of the present invention for radiolabeling with one or more diagnostic and/or therapeutic radionuclide and/or with a diagnostic radiotracer.

As discussed above, examples for diagnostic and/or therapeutic radionuclides are $^{68}$Ga, $^{177}$Lu, $^{64}$Cu, $^{89}$Zr and $^{18}$F.

As discussed above, an estradiol derivative radiolabeled with $^{18}$F can also be an estradiol derivative radiolabeled with $^{18}$F-FBA (fluorobenzaldehyde).

As discussed above, an estrone derivative radiolabeled with $^{18}$F can also be an estrone derivative radiolabeled with $^{18}$F-FBA (fluorobenzaldehyde).

As discussed above, an example for a diagnostic radiotracer is $^{18}$FDG (fluorodeoxyglucose).

Preferably, DOTA and NOTA-conjugated estradiol derivatives are radiolabeled with one or more diagnostic and/or therapeutic radionuclides, such as $^{68}$Ga, $^{177}$Lu, $^{64}$Cu, $^{89}$Zr.

Preferably, AoA-estradiol is radiolabeled with $^{18}$F or $^{18}$FDG (fluorodeoxyglucose).

Preferably, DOTA and NOTA-conjugated estrone derivatives are radiolabeled with one or more diagnostic and/or therapeutic radionuclides, such as $^{68}$Ga, $^{177}$Lu, $^{64}$Cu and $^{89}$Zr.

Preferably, AoA-estrone is radiolabeled with $^{1S}$F or $^{18}$FDG (fluorodeoxyglucose).

The present invention further provides the estradiol derivative of the present invention for use in medicine.

The present invention further provides the estrone derivative of the present invention for use in medicine.

The present invention further provides the estradiol derivative of the present invention for use in a method of imaging, diagnosis and/or treatment of breast cancer.

Preferably, the breast cancer is estrogen-receptor-positive breast cancer.

The present invention further provides the estrone derivative of the present invention for use in a method of imaging, diagnosis and/or treatment of breast cancer.

Preferably, the breast cancer is estrogen-receptor-positive breast cancer.

For imaging and/or diagnosis, the estradiol derivative or the estrone derivative used is preferably radiolabeled with one or more diagnostic radionuclide or a diagnostic radiotracer.

Examples for diagnostic radionuclides are $^{68}$Ga, $^{64}$Cu, $^{89}$Zr, $^{18}$F.

An example for a diagnostic radiotracer is $^{18}$F-FBA (fluorobenzaldehyde).

For treatment and therapy, the estradiol derivative or the estrone derivative used is preferably radiolabeled with a therapeutic radionuclide.

Examples for therapeutic radionuclides are $^{177}$Lu and $^{64}$Cu.

In a further aspect, the present invention also relates to the use of the estradiol derivatives) in accordance with the present invention for the manufacture of a medicament for the imaging, diagnosis and/or treatment of breast cancer, preferably estrogen-receptor-positive breast cancer.

In a further aspect, the present invention also relates to the use of the estrone derivative(s) in accordance with the present invention for the manufacture of a medicament for the imaging, diagnosis and/or treatment of breast cancer, preferably estrogen-receptor-positive breast cancer.

Imaging, Diagnosis and Treatment Methods

As outlined above, the present invention provides a method of imaging and/or diagnosis of breast cancer.

The breast cancer is preferably estrogen-receptor-positive breast cancer.

Said method comprises the step of:

administering a diagnostic amount of an estradiol derivative of the present invention or a diagnostic amount of an estrone derivative of the present invention to a subject.

A "diagnostic or tracer amount" of an estradiol derivative of the present invention or of an estrone derivative of the present invention refers to the amount which has to be administered to a subject in order to allow imaging and/or diagnosis in the desired high quality and high resolution. The skilled artisan will be able to determine a suitable diagnostic amount or tracer amount.

The route of administration can be intravenous.

For imaging and/or diagnosis, the estradiol derivative or the estrone derivative administered is preferably radiolabeled with a diagnostic radionuclide.

As discussed above, examples for diagnostic radionuclides are $^{68}$Ga, $^{64}$Cu, $^{89}$Zr and $^{18}$F.

As discussed above, an example for a diagnostic radiotracer is $^{18}$FDG (fluorodeoxyglucose).

As outlined above, the present invention provides a method of treatment of breast cancer. The breast cancer is preferably estrogen-receptor-positive breast cancer.

Said method comprises the step of:

administering a therapeutic amount of an estradiol derivative of the present invention or a therapeutic amount of an estrone derivative of the present invention to a subject in need thereof.

A "therapeutic amount" or a "therapeutically effective amount" of an estradiol derivative of the present invention or of an estrone derivative of the present invention refers to the amount which has to be administered to a subject in need thereof in order to achieve a desired therapeutic result or outcome. The skilled artisan will be able to determine said therapeutically effective amount and the suitable administration regimen.

The route of administration can be intravenous.

For treatment and therapy, the estradiol derivative or the estrone derivative administered is preferably radiolabeled with a therapeutic radionuclide.

As discussed above, examples for therapeutic radionuclides are $^{177}$Lu and $^{64}$Cu.

Preferably, DOTA and NOTA-conjugated estradiol/estrone derivatives are radiolabeled with one or more diagnostic and/or therapeutic radionuclides, such as $^{68}$Ga, $^{177}$Lu, $^{64}$Cu, $^{89}$Zr.

Preferably, AoA-estradiol/-estrone is radiolabeled with $^{18}$F or $^{18}$FDG (fluorodeoxyglucose).

In this invention, we present the novel solid-phase synthesis of estradiol derivatives and/or estrone derivatives wherein estradiol or estrone, respectively, is linked or conjugated with three different bifunctional groups, namely DOTA (1,4,7,10-tetraazacyclododecane-1,4,7,10-tetraacetic acid), NOTA (1,4,7-triazacyclononane-1,4,7-triacetic acid) and AoA (aminooxyacetic acid).

The DOTA and NOTA-conjugated estradiol derivatives and the DOTA and NOTA-conjugated estrone derivatives will allow the radiolabeling with a variety of medically useful diagnostic and therapeutic radionuclides (i.e., $^{68}$Ga, $^{177}$Lu, $^{64}$Cu, $^{89}$Zr, etc.) both for diagnosis and therapy.

Also, AoA-estradiol or AoA-estrone can be radiolabeled with $^{18}$F and $^{18}$FDG (fluorodeoxyglucose) via oxime functionality.

These new estradiol derivatives and/or estrone derivatives hold the ability to be the new theranostic agents for both imaging and therapeutic applications for estrogen receptors expressing primary and metastatic breast cancers. It is worth mentioning that while the FDA-approved $^{18}$F-FES only as a diagnostic radiotracer, the development of new theranostic-based estradiol and/or estrone radiopharmaceuticals will be beneficial for the efficient management of estrogen receptor-expressing breast cancers.

The invention discloses an easy and effective method of preparing estradiol derivatives and/or estrone derivatives. The solid-phase synthesis technique holds the distinct advantage of preparing estradiol/estrone as it can be synthesized efficiently in fewer synthetic steps with few purification steps. It has added advantages of solubility in aqueous solution, reagents used are less expensive, synthesis is rapid, and provides estradiol/estrone in good purity. The preparation method is novel as claimed for the convenient and economic preparation of DOTA-estradiol or NOTA-estradiol or AoA-estradiol/DOTA-estrone or NOTA-estrone or AoA-estrone.

The preparation method disclosed by present invention has the following beneficial effects:

i) the reagents used are less expensive,
ii) the reaction times are short,
iii) the required reagents of reaction consumes little,
iv) fewer preparation steps,
v) fewer purification steps,
vi) flexible synthesis approach,
vii) different bifunctional ligands can be conjugated,
viii) allows radiolabeling with different radionuclides,
ix) better solubility in the aqueous medium,
x) high purity,
xi) can used as a small-scale (milligrams) or large-scale (grams) preparation, and
xii) suitability for industrialized production.

FURTHER DESCRIPTION OF REFERRED EMBODIMENTS

Abstract

Fluoroestradiol is known as a clinically useful radiopharmaceutical in nuclear medicine as an estrogen-receptor (ER) ligand for investigating primary and metastatic breast carcinomas. The present invention relates to a novel and convenient preparation method of estradiol derivatives and/or estrone derivatives. The novel estradiol/estrone preparing method includes the following synthetic steps: 1, estrone is reacted with tert-butyl bromoacetate to prepare an estradiol tert-butyl acetate compound; 2, the tert-butyl estradiol acetate compound is treated with trifluoroacetic acid (TFA) in dichloromethane (DCM) to remove the tert-butyl group and to provide acetic acid estradiol; 3, acetic acid estradiol is reacted with the amino group of Lys(ivDde)-OH to prepare lysine acetic acid estradiol; 4, lysine acetic acid estradiol reacted with DOTA or NOTA or AoA to prepare DOTA/NOTA-AoA-estradiol derivatives or DOTA/NOTA-AoA-estrone derivatives for radiolabeling with both diagnostic and therapeutic radionuclides thus developing imaging- and treatment-based theranostic approach. When the estradiol or estrone is prepared with the present inventive method, the reagents used for the preparation are less expensive, the reaction time is short, the consumption of the reagents required by the reaction is small, fewer preparation and purification steps that give high yield preparation, and the novel estradiol/estrone preparing method is suitable for industrial production. This invention represents the first step on a path toward the design of radiolabeled estrogen-related compounds for the targeting of breast cancers.

Step (1) Preparation of a Preferred Acetic Acid Estradiol Precursor: Acetic Acid Estradiol 3.

A preferred preparation of acetic acid estradiol is presented in FIG. 2.

Estrone 1 (3.3 mmol, 900 mg) was dissolved in DMF (N,N-dimethylformamide). To this potassium carbonate ($K_2CO_3$, 550 mg, 1.2 equivalent) was added and the mixture was stirred for 3 minutes at room temperature. Tert-butyl bromoacetate 2 (500 µL, 1.0 equivalent) was then added followed by the addition of potassium iodide catalyst (KI, 65 mg, 0.1 equivalent). The reaction mixture was allowed to be stirred at ambient temperature for 24 hours to ensure quantitative coupling. The solvents were removed on a rotary evaporator, and the residue was diluted with ethyl acetate and transferred to a separatory funnel. The organic layer was washed with 2×20 mL of 10% sodium hydroxide solution (to remove unreacted estrone-OH) in the solvent extraction method. The organic layer was then separated and, dried with anhydrous sodium sulfate for 30 minutes. The solvent was filtered off using a filter paper and the filtrate was evaporated under reduced pressure to provide the alkylated product which was used directly in the next step.

Removal of ten-butyl protecting group: To remove the tert-butyl protecting group, the above alkylated compound was dissolved in 2 mL of dichloromethane (DCM) and 2 mL trifluoroacetic acid (TFA) was then slowly added. The resulting solution was stirred at ambient temperature for 2 hours. The solvents were removed on a rotary evaporator, and the resulting residue was dissolved in DCM (2 mL) and evaporated again. To the residue, diethyl ether (10 mL) was added and transferred to a 15 mL centrifuge tube. The acetic acid estradiol was precipitated as an off-white solid and was centrifuged and washed with diethyl ether (3×10 mL). Finally, the acetic acid estradiol was dried overnight in a desiccator to yield the desired compound as a solid. The purity of this acetic acid estradiol 3 product was checked by reversed-phase high-performance liquid chromatography and its structural identity by liquid chromatography-mass spectrometry analysis. Yield=60%; $C_{20}H_{24}O_4$=MW: 328.4

LC-MS: m/z calcd for $C_{20}H_{24}O_4$ 328.4; found, 328.8 $[M+H]^+$.

Steps (2) to (5) Preparation of Preferred Estradiol-Lysine Derivatives: Estradiol-Lysine-DOTA, Estradiol-Lysine-NOTA and Estradiol-Lysine-AoA by Solid-Phase Synthesis.

A preferred solid-phase synthesis for the preparation of estradiol derivatives comprises 4 main steps (shown in FIGS. 3A-3C):

a) The coupling of estradiol to Fmoc-Lys (ivDde)-Wang Resin
b) Removal of the ivDde protecting group
c) The coupling of estradiol to DOTA or NOTA or AoA
d) Removal of estradiol from the resin by the TFA-cleavage Solid-phase synthesis of the estradiol derivatives was started by utilizing the commercially available Fmoc-Lys (ivDde)-wang resin using the peptide synthesis glass reaction vessel (Peptides International, Louisville, USA). For solid-phase synthesis, standard Fmoc (9-fluorenylmethyloxycarbonyl) chemistry was employed on a 0.2 mmol scale. The wang-resin was soaked in DMF for 60 minutes and in DCM for 30 minutes. The solvent was drained and the Fmoc protecting group of the lysine was removed by treating the resin with 20% piperidine solution in DMF followed by standard washing with DMF (3×3 mL) and DCM (3×3 mL). To attach estradiol to the wang resin, the acetic acid estradiol 3 was first preactivated at its α-carboxylic function by the use of an activating reagent, HBTU (O-benzotriazol-1-yl)-1,1,3,3-tetramethyluronium hexafluorophosphate) in the presence of a base DIEA (diisopropylethylamine) and then allowed to react for 60 minutes at the ambient temperature with the resin-bound amino group of lysine to form an amide bond. The completion of the coupling was confirmed by the Kaiser ninhydrin test. At this point, the epsilon ivDde protecting group of the lysine was deprotected using 2% hydrazine monohydrate in DMF (3×3 mL) followed by standard washings with DMF (3×3 mL) and DCM (3×3 mL) to allow conjugation with a bifunctional group for the radiolabeling purpose (i.e., DOTA or NOTA or AoA), as described below.

For the preparation of DOTA (1,4,7,10-tetraazacyclododecane-1,4,7,10-tetraacetic acid) coupled with estradiol, commercially available DOTA-tris-(t-Bu ester) was first preactivated with HBTU (2 equivalent) and DIEA (4 equivalent) in DMF for 5 minutes before the conjugation with the resin. The coupling mixture was allowed to react for 4 hours at the ambient temperature and the completion of the reaction was confirmed by the negative Kaiser test. DOTA-estradiol was obtained as a solid product.

For the preparation of NOTA (1,4,7-triazacyclononane-1,4,7-triacetic acid) conjugation with estradiol, commercially available NOTA-bis-(t-Bu ester) (2 equivalent) was first preactivated with HBTU (2 equivalent) and DIEA (4 equivalent) in DMF for 5 minutes before the conjugation with the resin. The coupling mixture was allowed to react for 4 hours at the ambient temperature and the completion of the reaction was confirmed by the negative Kaiser test. NOTA-estradiol was obtained as a solid product.

For the coupling to tert-butyloxycarbonyl-aminooxy acetic acid (Boc-AoA), it was first preactivated with HBTU (2 equivalent) and DIEA (4 equivalent) in DMF for 5 minutes before the conjugation with the resin. The coupling reaction was completed after 2 hours, as determined by the negative Kaiser test. The resin was washed with DMF (3×3 mL), DCM (3×3 mL), and ether (2×3 mL) and dried overnight in a desiccator.

Removal of estradiol from the resin and side-chain deprotection: Finally, the estradiol analogs, such as DOTA-estradiol, NOTA-estradiol, and Boc-aminooxy acetic acid estradiol were cleaved from the resin along with other side-chain protecting groups by reacting the resin with a cleavage cocktail (~5 mL) of trifluoroacetic acid (TFA)/triisopropylsilane/water (95%:2.5%:2.5%, v/v) for 4 hours at ambient temperature. The resin was removed by filtration and TFA was evaporated by rotary evaporator. To the residue, cold diethyl ether was added to precipitate the desired product which was then transferred to a 15 mL centrifuge vial and centrifuged thrice at 7200 RPM to form a pellet of the target product. The ether was decanted and the DOTA/NOTA/AoA-estradiol products were allowed to dry overnight in a desiccator to yield the desired estradiol analog as a solid. The purity of these estradiol compounds was checked by reversed-phase high-performance liquid chromatography and its structural identity by mass spectrometry analysis.

The structures of the newly synthesized DOTA/NOTA/AoA-estradiol derivatives were confirmed by mass spectrometry analyses performed on Agilent 6125 single quadrupole liquid chromatography/mass spectrometry system (LC/MS) (Agilent Technologies, Santa Clara, CA, USA) using an eluent of 0.1% formic acid/29.95% water/69.95% acetonitrile at a flow rate of 0.3 mL/min. It was found that the experimentally determined molecular weights correlated well with the theoretically calculated values (FIG. 2).

For DOTA-estradiol:

Yield=40%; $C_{42}H_{63}N_6O_{12}$=MW: 843.5

LC-MS: m/z calcd for $C_{42}H_{63}N_6O_{12}$ 843.5; found, 844.5 $[M+H]^+$.

For NOTA-estradiol:

Yield=37%; $C_{38}H_{59}N_6O_9$=MW: 743.5

LC-MS: m/z calcd for $C_{38}H_{59}N_6O_9$ 743.5; found, 744.6 $[M+H]^+$.

For AoA-estradiol:

Yield=39%; $C_{28}H_{40}N_3O_7$=MW: 530.3

LC-MS: m/z calcd for $C_{28}H_{40}N_3O_7$ 530.3; found, 531.7 $[M+H]^+$.

In summary, adopting a novel estradiol and/or estrone preparation method provided by this invention to prepare estradiol derivatives and/or estrone derivatives suitable for radiolabeling by solid-phase synthesis, the reagents that preparation uses are cheap, reaction time is short, and the required reagents of the reaction consume little, fewer preparation and purification steps, flexible synthetic approach, suitable for industrialized production. This invention is the first step toward the development of estradiol/estrone derivatives and the scope of the invention can be extended for its application in the imaging and treatment of estrogen-receptor-positive breast carcinomas using the newly synthesized estradiol derivatives.

The following examples and drawings illustrate the present invention without, however, limiting the same thereto.

(a) $K_2CO_3$, KI, DMF, 23° C., 24 h;

(b) TFA, DCM, 23° C., 2 h.

Figure 1:
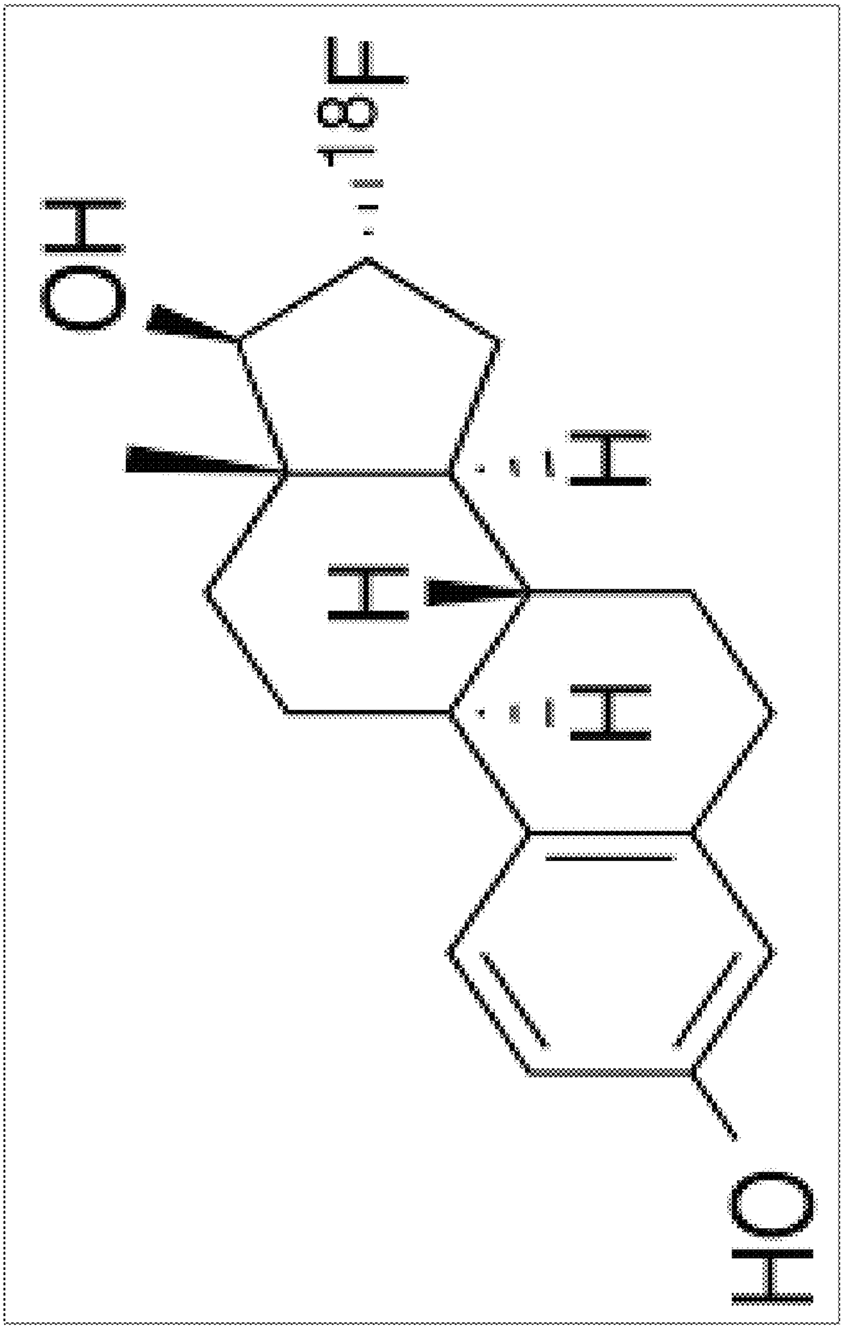
FIG. 1. $^{18}$F-fluoroestradiol ($^{18}$F-FES)
Figure 2:
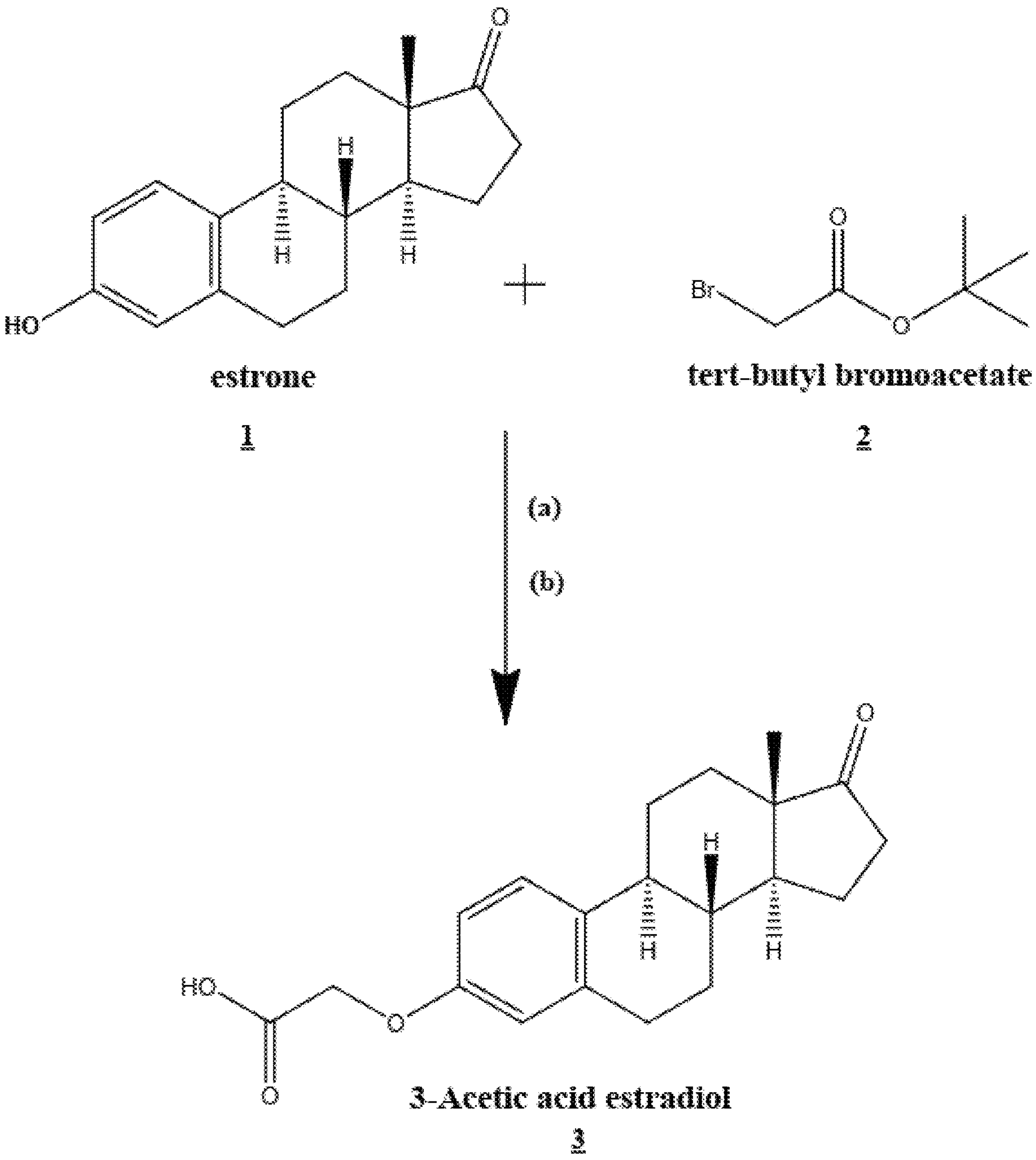
FIG. 2. Scheme of the preparation of 3-acetic acid estradiol.
Figure 3A:
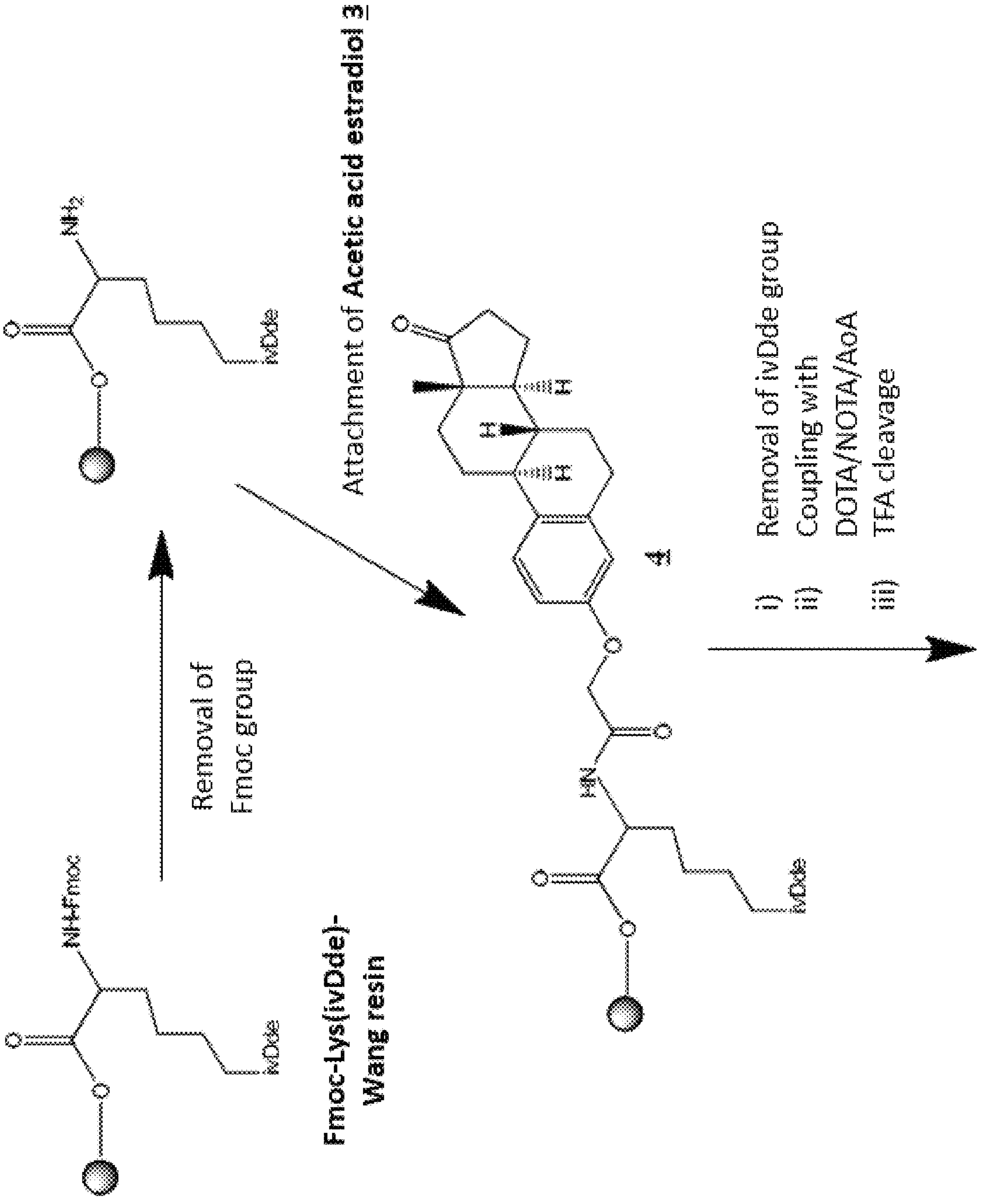
Figure 3B:
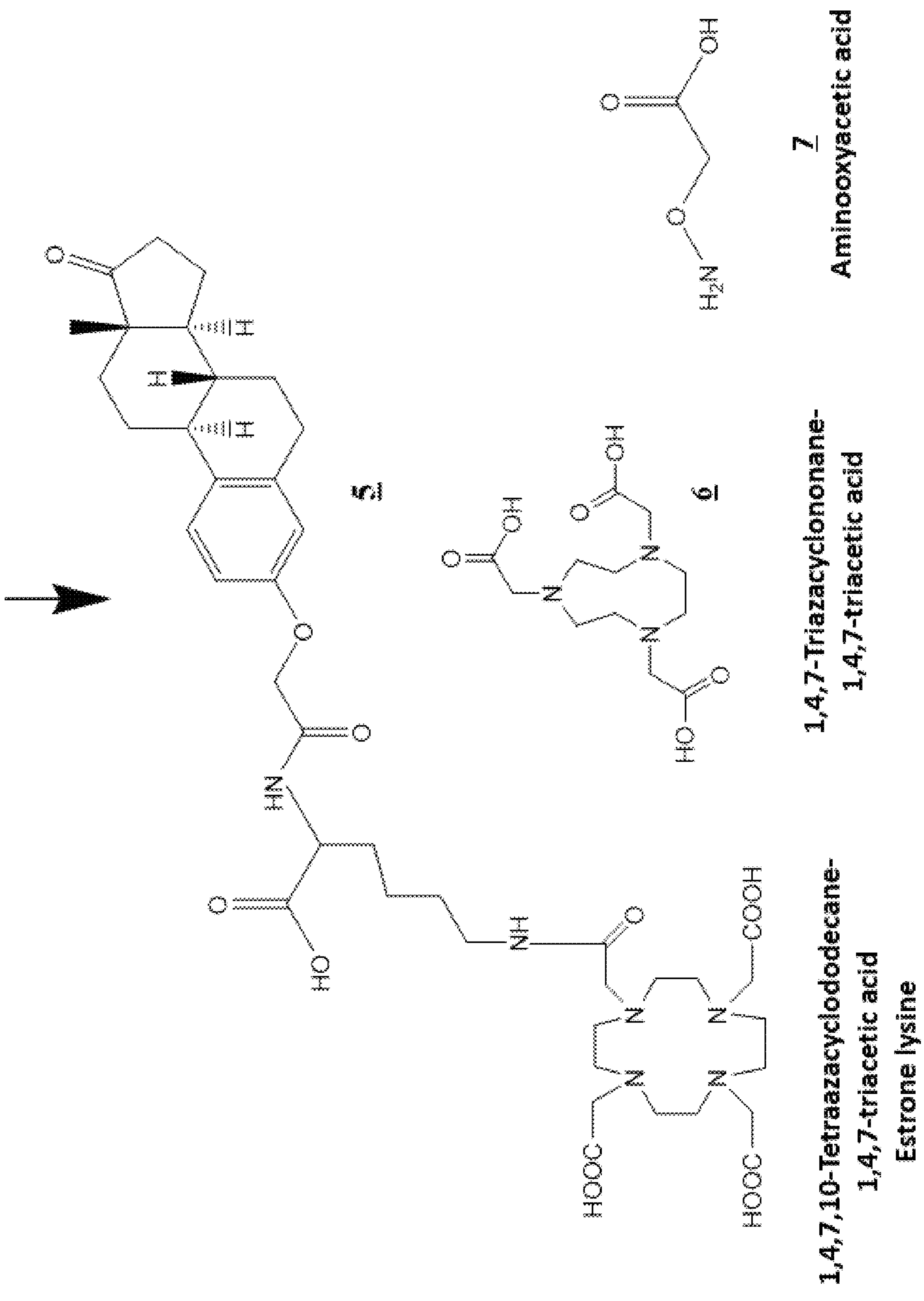
Figure 3C:
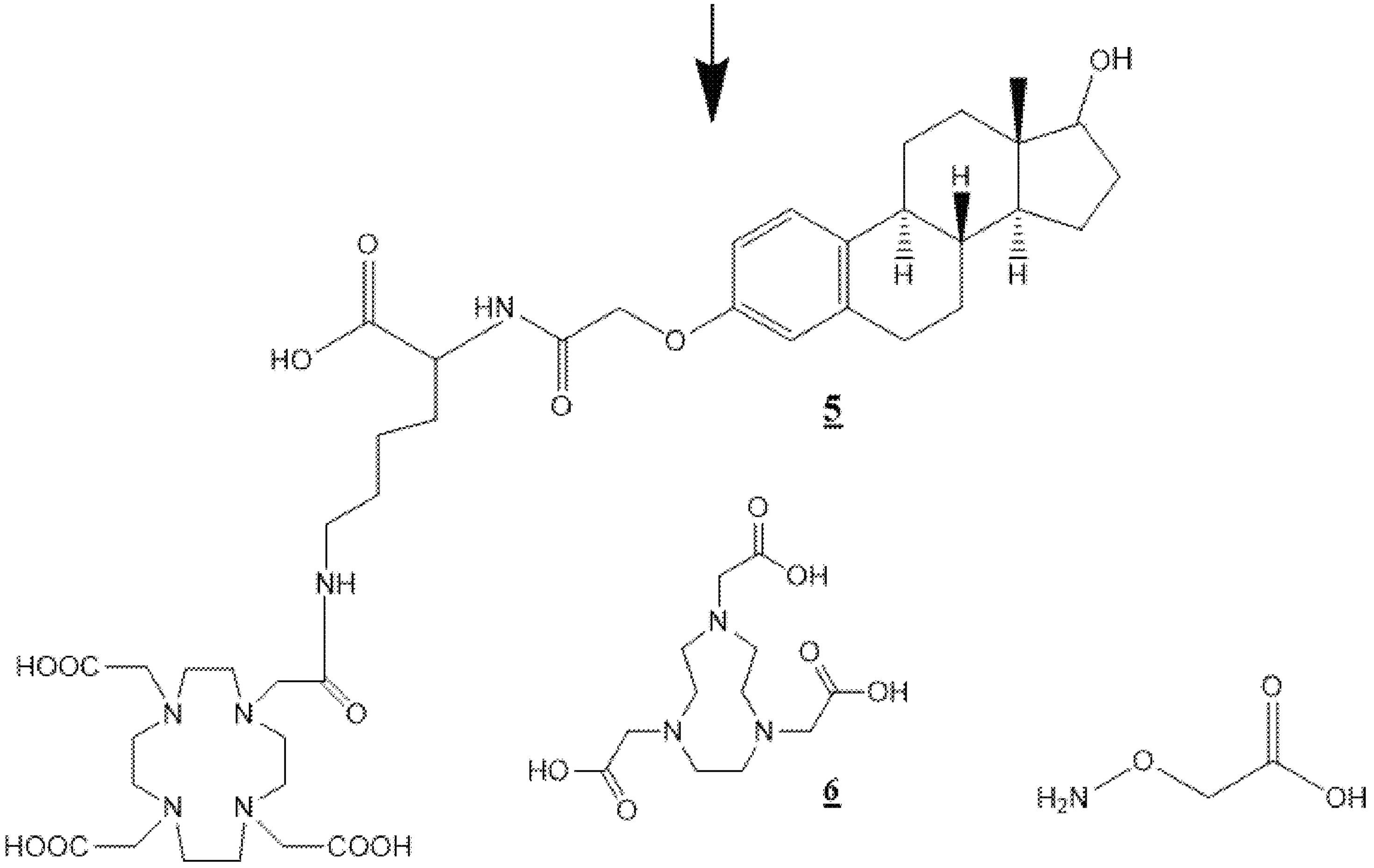
Figure 4A:
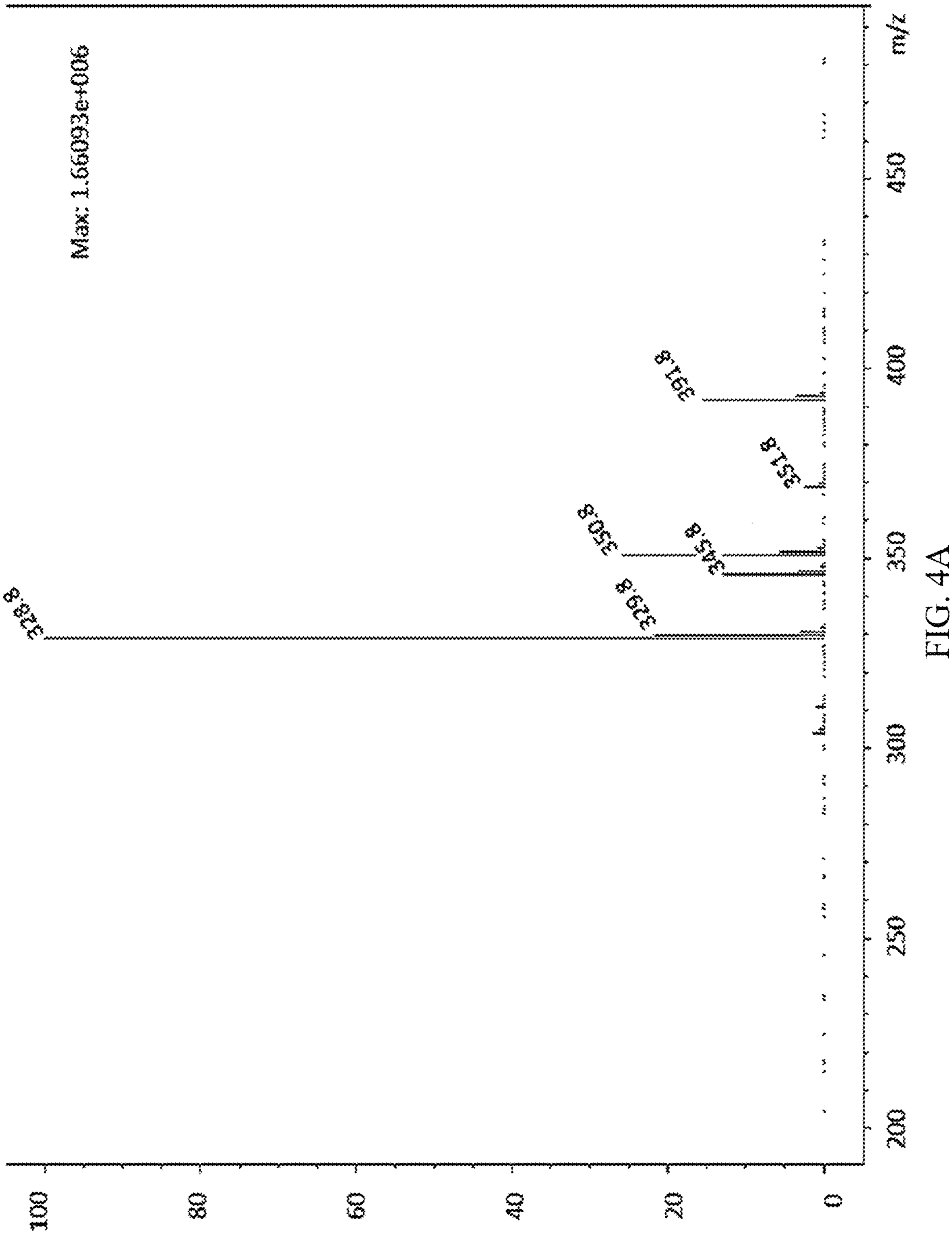
Figure 4B:
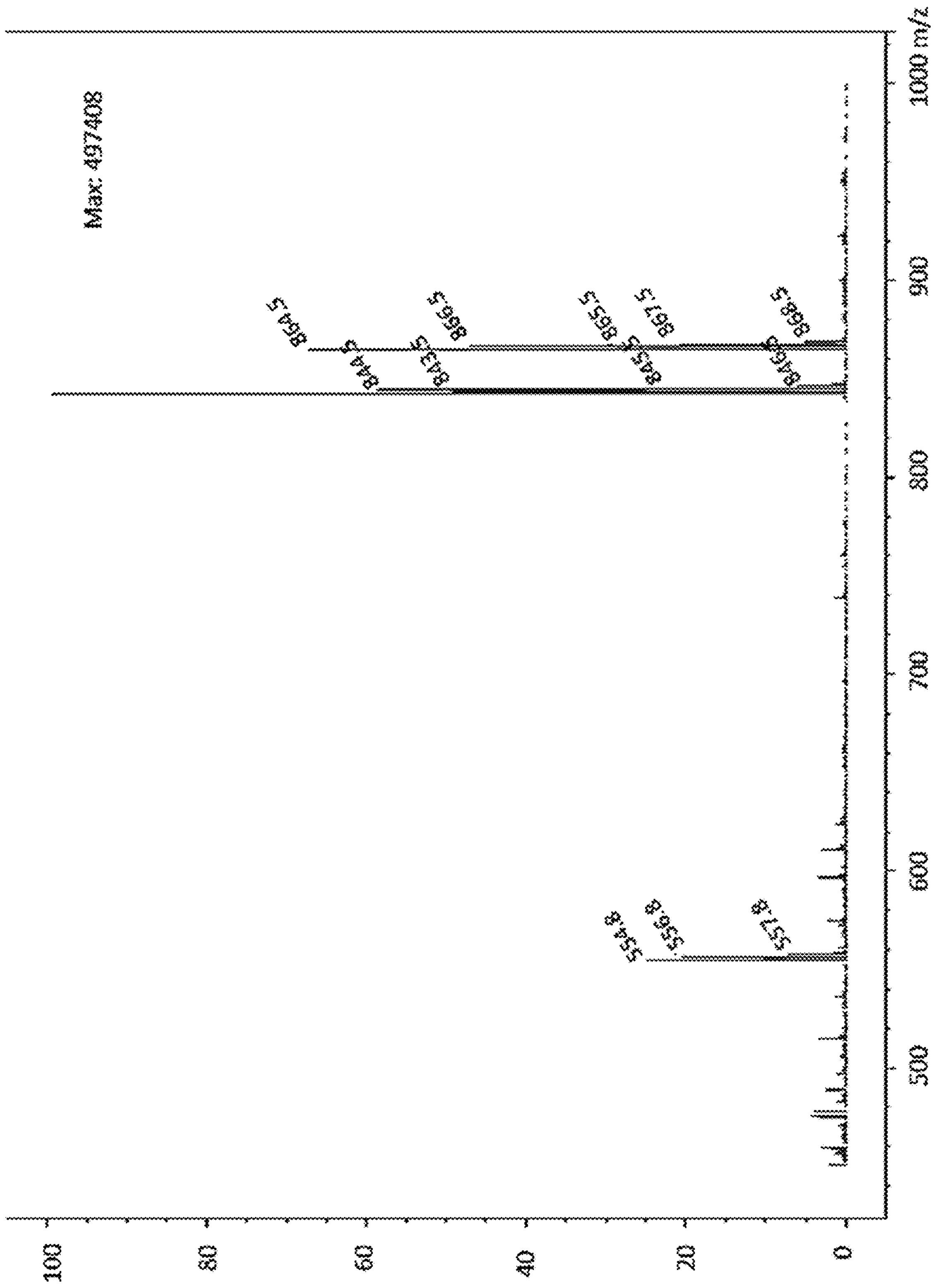
Figure 4C:
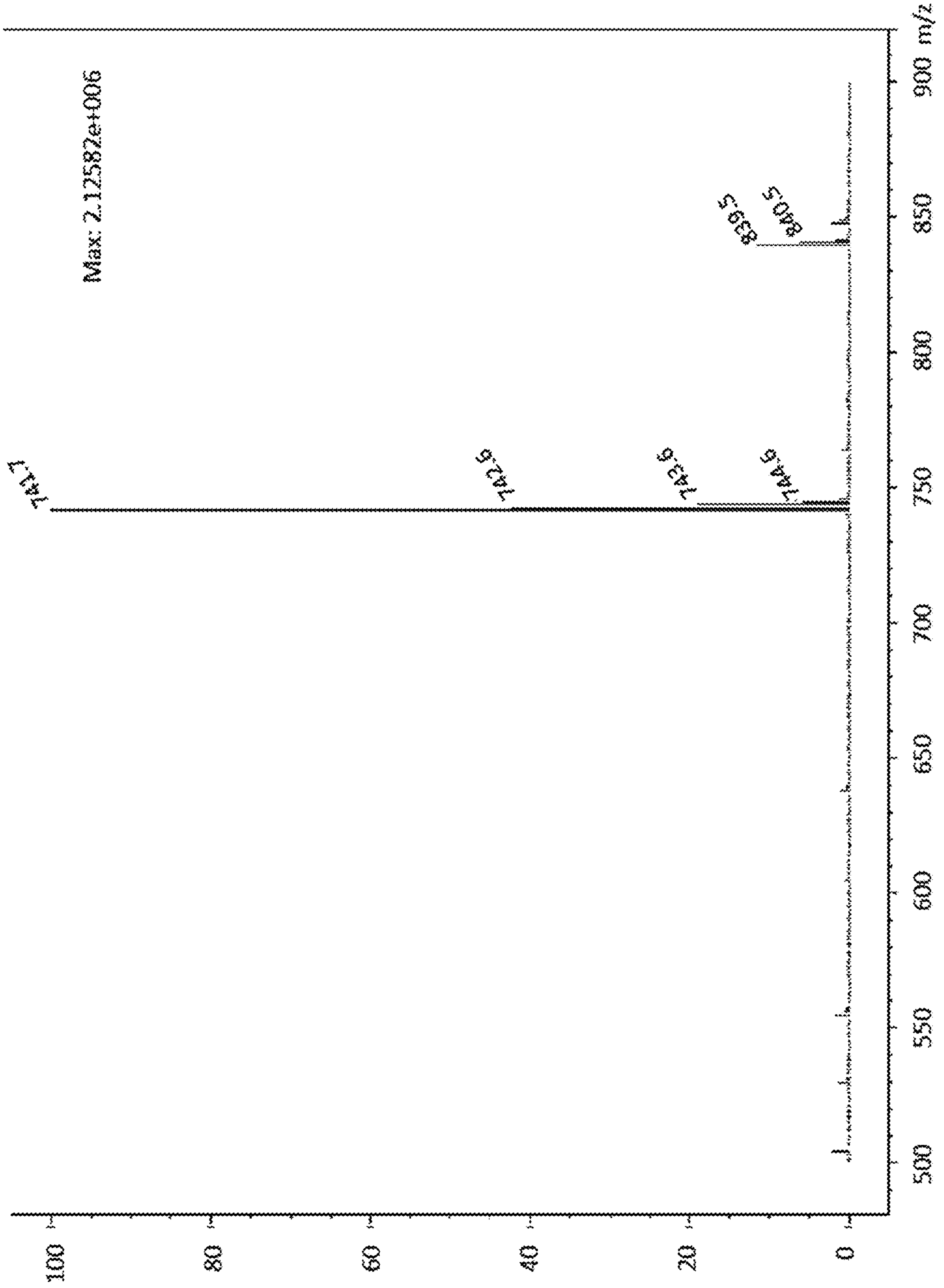
Figure 4D:
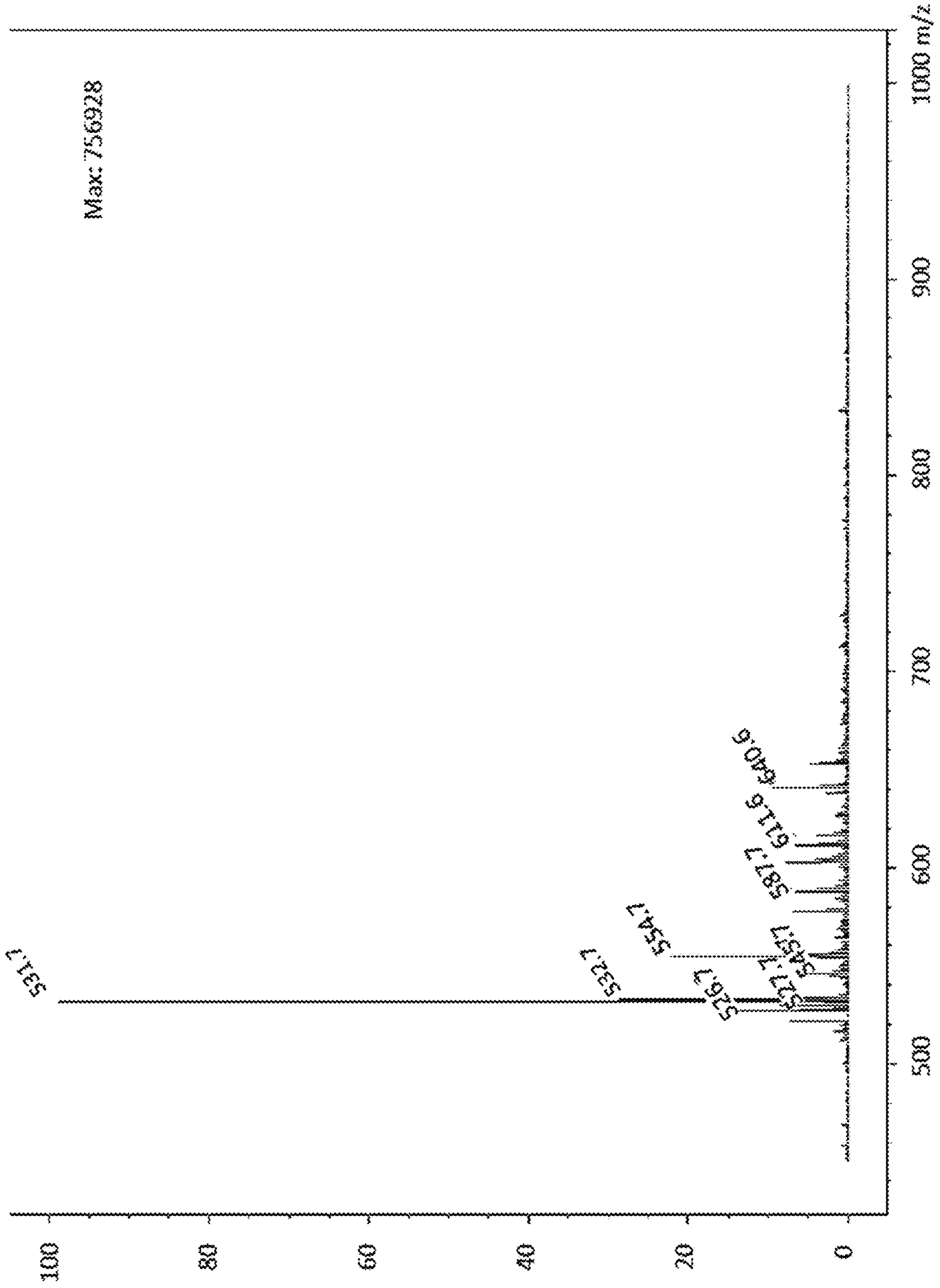

FIGS. 3A-3C. Scheme of the preparation of DOTA/NOTA/AoA-estrone as well as DOTA/NOTA/AoA-estradiol by solid phase synthesis.

(3A) and (3B) Scheme of the preparation of DOTA/NOTA/AoA-estrone by solid phase synthesis.

(3C) DOTA/NOTA/AoA-estradiol derivatives.

FIGS. 4A-4D. Mass spectrometry analysis of the precursor and the estradiol derivatives.

(4A) Mass spectrometry of 3-acetic acid estradiol.

LC-MS: m/z calcd for $C_{20}H_{24}O_4$ 328.4; found, 328.8 $[M+H]^+$.

(4B) Mass spectrometry of DOTA-estradiol.

LC-MS: m/z calcd for $C_{42}H_{63}N_6O_{12}$ 843.5; found, 844.5 $[M+H]^+$ (4C) Mass spectrometry of NOTA-estradiol.

LC-MS: m/z calcd for $C_{38}H_{59}N_6O_9$ 743.5; found, 744.6 $[M+H]^+$.

(4D) Mass spectrometry of AoA-estradiol.

LC-MS: m/z calcd for $C_{28}H_{40}N_3O_7$ 530.3; found, 531.7 $[M+H]^+$.

EXAMPLES

1. Materials and Methods

All chemicals, solvents and reagents for the synthesis of estradiol derivatives were procured from different commercial sources and used without further purification. $^{177}$Lu radionuclide and $^{68}$Ge/$^{68}$Ga generator were bought from ITG Isotope Technologies Garching GmbH, Germany.

$^{18}$FDG, $^{64}$Cu and $^{89}$Zr radionuclides are produced at on-site facility of the Cyclotron and Radiopharmaceuticals Department.

Solid-phase synthesis of the estradiol derivatives was started by utilizing the commercially available Fmoc-Lys (ivDde)-wang resin using the peptide synthesis glass reaction vessel (Peptides International, Louisville, USA).

The structures of the newly synthesized DOTA/NOTA/AoA-estradiol derivatives were confirmed by mass spectrometry analyses performed on Agilent 6125 single quadrupole liquid chromatography/mass spectrometry system (LC/MS) (Agilent Technologies, Santa Clara, CA, USA) using an eluent of 0.1% formic acid/29.95% water/69.95% acetonitrile at a flow rate of 0.3 mL/min.

The features disclosed in the foregoing description, in the claims and/or in the accompanying drawings may, both separately and in any combination thereof, be material for realizing the invention in diverse forms thereof.

REFERENCES

Allegra, J. C. Distribution, frequency, and quantitative analysis of estrogen, progesterone, androgen, and glucocorticoid receptors in human breast cancer. *Cancer Res* 29, 1447-1454 (1979).

Allison, K. H. et al. Estrogen and Progesterone Receptor Testing in Breast Cancer: ASCO/CAP Guideline Update. *J. Clin Oncol.* 38, 1346-1366 (2020).

Bafaloukos, D. et al. Neo-adjuvant therapy in breast cancer. *Ann Oncol* 16, 11174-ii181 (2005).

Blamey, R. W. et al. ONCOPOOL—A European database for 16,944 cases of breast cancer. *Eur J Cancer.* 46, 56-71(2010).

Brookes, 2021: Fluoroestradiol F 18—a molecular marker becomes commercially available for PET imaging in metastatic breast cancer. *Molecular Imaging*—Siemens; https://www.siemens-healthineers.com (https://www.siemens-healthineers.com/en-pk/medical-imaging/molecular-imaging/mi-clinical-corner/scientifc-and-clinical-publications/cerianna-scientfc-insight)

Cardoso F, et al. Characterization of male breast cancer: results of the EORTC 10085/TBCRC/BIG/NABCG. International Male Breast Cancer Program. *Ann Oncol.* 29, 405-417 (2018).

CERIANNA™ (fluoroestradiol F 18) Injection, for intravenous use Initial U.S. Approval: 2020. Reference ID: 4610145-Accessdata.fda.gov.

DiZio J. P. et al. Progestin-rhenium complexes: metal-labeled steroids with high receptor binding affinity, potential receptor-directed agents for diagnostic imaging or therapy. *Bioconjug Chem.* 2, 353-366 (1991).

Fani, M. et al. Radiolabeled peptides: Valuable tools for the detection and treatment of cancer. *Theranostics* 2, 481-501 (2012).

Gradishar, W, et al. NCCN Clinical practice guidelines in oncology. Breast cancer, version 5. 2020. https://www.nccn.org/professionals/physician_gls/default.aspx. (2020).

Katzenellenbogen, J. A. et al. The development of estrogen and progestin radiopharmaceuticals for imaging breast cancer. *Anticancer Res.* 17, 1573-1576 (1997).

Katzenellenbogen, J. A. PET Imaging Agents (FES, FFNP, and FDHT) for Estrogen, Androgen, and Progesterone Receptors to Improve Management of Breast and Prostate Cancers by Functional Imaging. *Cancers* 12 (2020).

Kiesewetter, D. O. et al. Preparation of Four Fluorine-18 Labeled Estrogens and their selective uptakes in target tissues of immune rats. *J. Nucl. Med.* 25, 1212-1221 (1984).

Lau, J. et al. Insight into the development of PET radiopharmaceuticals for oncology. *Cancers* 12, 1312 (2020).

Nayak, T. K. et al. Preclinical Development of a Neutral, Estrogen Receptor-Targeted, Tridentate $^{99m}$Tc(I)-Estradiol-Pyridin-2-yl Hydrazine Derivative for Imaging of Breast and Endometrial Cancers. *J. Nucl. Med* 49, 978-986 (2008).

Ramesh, C. et al. Linkage effects on binding affinity and activation of GPR30 and estrogen receptors ERα/β with tridentate pyridin-2-yl hydrazine tricarbonyl-Re/99mTc (I) chelates. *J. Am. Chem. Soc.* 128, 14476-14477 (2006).

Shi, J. et al. Rapid synthesis of [$^{18}$F]-fluoroestradiol: remarkable advantage of microwaving over conventional heating. *J. Labelled Comp. Radiopharm.* 57, 730-736 (2014).

Tejeria, M. E. et al. Development and characterization of a $^{99m}$Tc-tricarbonyl-labelled estradiol derivative obtained by "Click Chemistry" with potential application in estrogen receptors imaging. *J. Labelled Comp. Radiopharm.* 60, 521-527 (2017).

Thompson, E. B. et al. Steroid receptors and the management of cancer. Vol 1, Boca Raton, Florida, CRC Press, pp 1-248 (1979).

Veronesi, U. et al. Breast cancer. *Lancet.* 365, 1727-1741 (2005).

Xia, X. et al. $^{99m}$Tc-labeled estradiol as an estrogen receptor probe: Preparation and preclinical evaluation. *Nucl. Med Biol.* 43, 89-96 (2016).

The invention claimed is:

1. A method of preparing an estradiol derivative and/or estrone derivative for radiolabeling, comprising the steps of (1) preparing an acetic acid-estradiol precursor;

(2) coupling the acetic acid-estradiol precursor obtained in step (1) to a solid phase synthesis resin, wherein said resin is suitable for Fmoc (9-fluorenylm-ethyl-oxycarbonyl)-solid phase synthesis and carries Fmoc-lysine with a protecting group at the lysine side chain;

(3) removing the protecting group at the lysine side chain;

(4) coupling a bifunctional group for radiolabeling to the lysine side chain; and (5) removal of the estradiol derivative and/or the estrone derivative from the resin.

2. The method of claim 1, wherein step (1) comprises reacting estrone and tert-butyl bromoacetate.

3. The method of claim 2, wherein in step (1) estrone and tert-butyl bromoacetate are reacted in the presence of potassium carbonate ($K_2CO_3$) and potassium iodide (KI).

4. The method of claim 2, wherein at the end of step (1) the tert-butyl protecting group is removed from the acetic acid-estradiol precursor.

5. The method of claim 1, wherein the solid phase synthesis resin is Wang resin.

6. The method of claim 1, wherein the protecting group at the Lys side chain resin is ivDde (4,4-dimethyl-2,6-dioxo-cyclohex-1-ylidene)-3-methylbutyl-) and the resin is Fmoc-Lys(ivDde)-Wang resin.

7. The method of claim 1, wherein before the coupling of step (2), the acetic acid-estradiol precursor is preactivated at its α-carboxylic function by using an activating reagent.

8. The method of claim 1, wherein said activating reagent is HBTU (O-benzotriazol-1-yl)-1,1,3,3-tetramethyluronium hexafluorophosphate) which is used in the presence of a base.

9. The method of claim 8, wherein the base is DIEA (diisopropylethylamine).

10. The method of claim 1, wherein the bifunctional group for radiolabeling is selected from DOTA (1,4,7,10-tetraaza-cyclododecane-1,4,7,10-tetraacetic acid), NOTA (1,4,7-tri-azacyclononane-1,4,7-triacetic acid) and AoA (aminooxy acetic acid).

11. The method of claim 1, wherein in step (4) for coupling the bifunctional group for radiolabeling to the Lys side chain DOTA-tris-(t-Bu ester), NOTA-bis-(t-Bu ester) or Boc-AoA is used, wherein said DOTA-tris-(t-Bu ester), NOTA-bis-(t-Bu ester) or Boc-AoA is preactivated.

12. The method of claim 11, wherein the DOTA-tris-(t-Bu ester), NOTA-bis-(t-Bu ester) or Boc-AoA is preactivated with HBTU and DIEA.

13. The method of claim 1, wherein at least one of steps (1) to (5) is carried out at a temperature in the range from about 18 to about 30° C.

14. The method of claim 1, wherein all steps are carried out at a temperature in the range from about 18 to about 30° C.

15. The method of claim 1, further comprising the step of (6) radiolabeling the estradiol derivative and/or estrone derivative obtained in step (5) with one or more diagnostic and/or therapeutic radionuclides, and/or with one or more diagnostic radiotracers.

16. The method of claim 15, wherein the one or more diagnostic and/or therapeutic radionuclides are selected from $^{68}$Ga, $^{177}$Lu, $^{64}$Cu, $^{89}$Zr, $^{18}$F, $^{18}$FDG and $^{18}$F-FBA (fluorobenzaldehyde).

17. The method of claim 15, wherein the diagnostic radiotracer is $^{18}$FDG (fluorodeoxyglucose).

18. An estradiol derivative or an estrone derivative selected from DOTA-estradiol, NOTA-estradiol, AoA-estradiol, DOTA-estrone, NOTA-estrone and AoA-estrone.

19. The estradiol derivative or the estrone derivative of claim 18, which is selected from DOTA-estradiol-lysine, NOTA-estradiol-lysine, AoA-estradiol-lysine, DOTA-estrone-lysine, NOTA-estrone-lysine and AoA-estrone-lysine.

20. The estradiol derivative or the estrone derivative of claim 18, which further comprises one or more diagnostic and/or therapeutic radionuclides, and/or one or more diagnostic radiotracers.

21. The estradiol derivative or the estrone derivative of claim 20, wherein the one or more diagnostic and/or therapeutic radionuclides are selected from $^{68}$Ga, $^{177}$Lu, $^{64}$Cu, $^{89}$Zr, $^{18}$F, $^{18}$FDG and $^{18}$F-FBA (fluorobenzaldehyde).

22. The estradiol derivative or the estrone derivative of claim 20, wherein the diagnostic radiotracer is $^{18}$FDG (fluorodeoxyglucose).

23. A method of imaging and/or diagnosis of breast cancer, comprising the step of:

administering a diagnostic amount of an estradiol derivative or an estrone derivative of claim 18 to a subject.

24. The method of claim 23, wherein the breast cancer is estrogen-receptor-positive breast cancer.

25. A method of imaging and/or diagnosis of breast cancer, comprising the step of:

administering a diagnostic amount of an estradiol derivative or an estrone derivative of claim 18 to a subject, wherein the estradiol derivative or the estrone derivative further comprises one or more diagnostic radionuclides or one or more diagnostic radiotracers.

26. A method of treatment of breast cancer, comprising the step of:

administering a therapeutic amount of an estradiol derivative or an estrone derivative of claim 18 to a subject in need thereof.

27. The method of claim 26, wherein the breast cancer is estrogen-receptor-positive breast cancer.

28. A method of treatment of breast cancer, comprising the step of:

administering a therapeutic amount of an estradiol derivative or an estrone derivative of claim 18 to a subject in need thereof, wherein the estradiol derivative or the estrone derivative further comprises one or more therapeutic radionuclides.

* * * * *